US00PP17457P3

(12) United States Plant Patent
Monet

(10) Patent No.: US PP17,457 P3
(45) Date of Patent: Feb. 27, 2007

(54) PEACH TREE NAMES 'S 5848'

(50) Latin Name: ***Prunus persica* L. Batsch**
Varietal Denomination: S 5848

(75) Inventor: René Francois Monet, Villenave D'Ornon (FR)

(73) Assignee: Agri-Obtentions SA, Guyancourt Cedex (FR)

( * ) Notice: Subject to any disclaimer, the term of this patent is extended or adjusted under 35 U.S.C. 154(b) by 7 days.

(21) Appl. No.: 11/013,507

(22) Filed: Dec. 15, 2004

(65) Prior Publication Data

US 2005/0198716 P1 Sep. 8, 2005

Related U.S. Application Data

(60) Provisional application No. 60/531,537, filed on Dec. 18, 2003.

(51) Int. Cl.
*A01H 5/00* (2006.01)

(52) U.S. Cl. ..... Plt./198

(58) Field of Classification Search ..... Plt./198, Plt./194, 195, 196, 197
See application file for complete search history.

(56) References Cited

U.S. PATENT DOCUMENTS

PP5,123 P * 10/1983 Bailey et al. ..... Plt./196
PP12,157 P2 * 10/2001 Slaughter et al. ..... Plt./197
PP13,352 P2 * 12/2002 Sherman ..... Plt./197

OTHER PUBLICATIONS

New UF Peach Variety has Strange Shape and Sweet Taste, University of Florida News, Jun. 8, 2001 [online], [retrieved on Mar. 14, 2006]. Retrieved from the Internet <http://news.ufl.edu/2001/06/08/ufo–peach/> 2pages.*

Sales of Freestone Peach Trees for Commercial Planting in California, including Graftings [online], [retrieved on Sep. 29, 2005]. Retrieved from the Internet <http://www.eatcaliforniafruit.com/growers–shippers/reports–bulletins/pdf/Peach_Tree_Sales_03.pfd> 5pages.*

* cited by examiner

*Primary Examiner*—Kent Bell
*Assistant Examiner*—June Hwu
(74) *Attorney, Agent, or Firm*—Stratton Ballew PLLC

(57) ABSTRACT

A new cultivar of peach tree (*Prunus persica* L. Batsch) named 'S-5848' is disclosed. The new cultivar is notable for its large, yellow fleshed, high quality fruit.

3 Drawing Sheets

Latin name of the genus and species of the plant claimed: *Prunus persica* L. Batsch.
Variety denomination: 'S 5848'.

BACKGROUND OF THE INVENTION

The invention relates to the field of peach trees. More specifically, the invention is a new and distinct cultivar of peach tree *Prunus persica* L. Batsch named 'S 5848'. The new peach tree 'S 5848' is a product of the breeding program at Angers, France. 'S 5848' was one of several seedlings resulting from a cross of unknown parents. 'S 5848' was asexually propagated by budding at Angers, France, and has been observed to remain true to type over successive asexually propagated generations.

BRIEF DESCRIPTION OF THE INVENTION

'S 5848' was selected for its suitability as a commercial peach tree cultivar. Fruit of the 'S 5848' cultivar matures in late August in central Washington state, and is notable for its oblate shape and yellow orange flesh. The characteristics which distinguish 'S 5848' from other related varieties are set forth in Table 1.

TABLE 1

Comparison of 'S 5848' to Other Known Varieties (measurements given are approximate)

| Variety | Fruit Size - Diameter | Fruit Size - Height | Shape | Flesh Color | Harvest Date |
|---|---|---|---|---|---|
| S 5848 | 8 cm | 4.5 cm | Broad oblate | Orange 21B | 8/20–8/30 (Central Washington) |
| NJ. F-2 | 5.5 cm | 2.5 cm | Broad oblate | White | 7/25–8/5 (New Jersey) |
| Burpeachtwo -(USPP 12157) | 8 cm | 7.5 cm | Oblate | Yellow orange 16A–D to reddish orange 45B | 8/1–8/10 (Central California) |
| UFO (USPP 13352) | 6.3 cm | 2.5 cm | Flat oval | Yellow | 5/20–5/30 (Florida) |

DETAILED BOTANICAL DESCRIPTION

Figure 1:
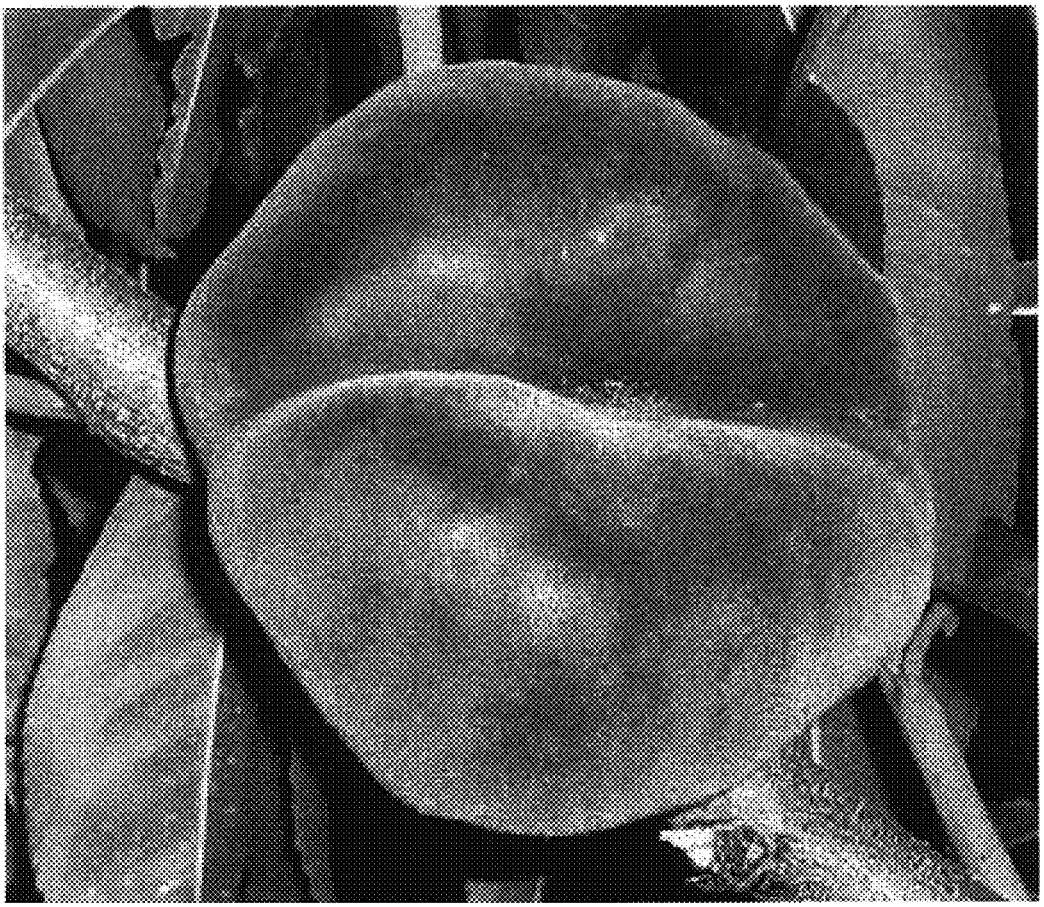
FIG. 1 shows a fruit of the new variety.
Figure 2:
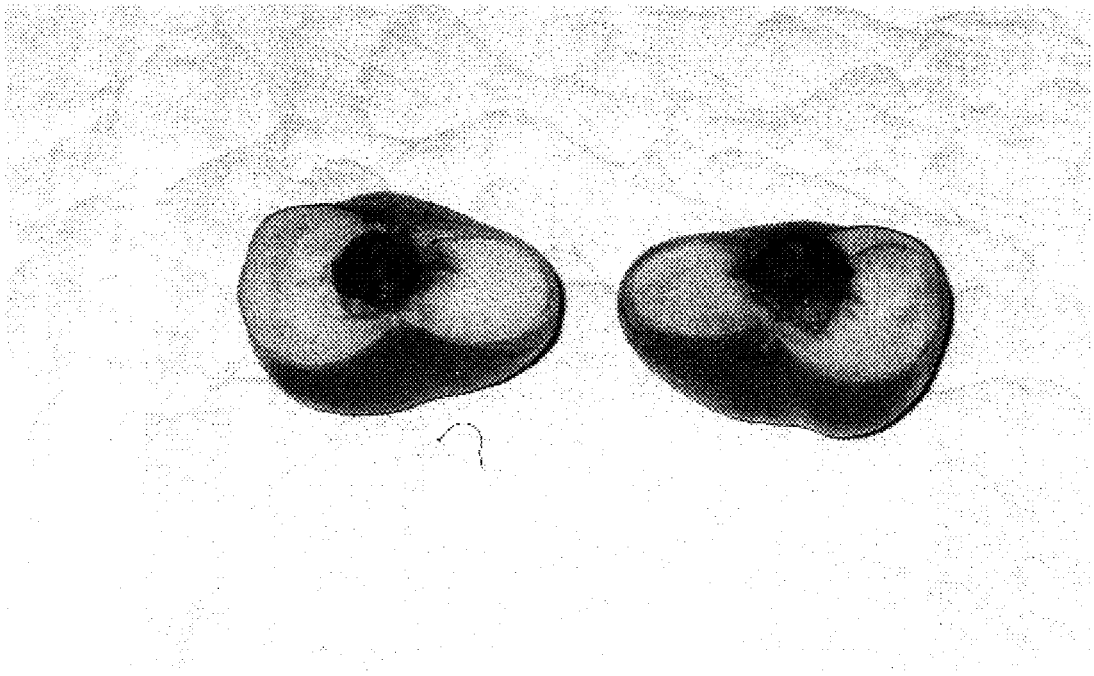
FIG. 2 shows a fruit of the new variety, including the flesh and stone thereof.
Figure 3:
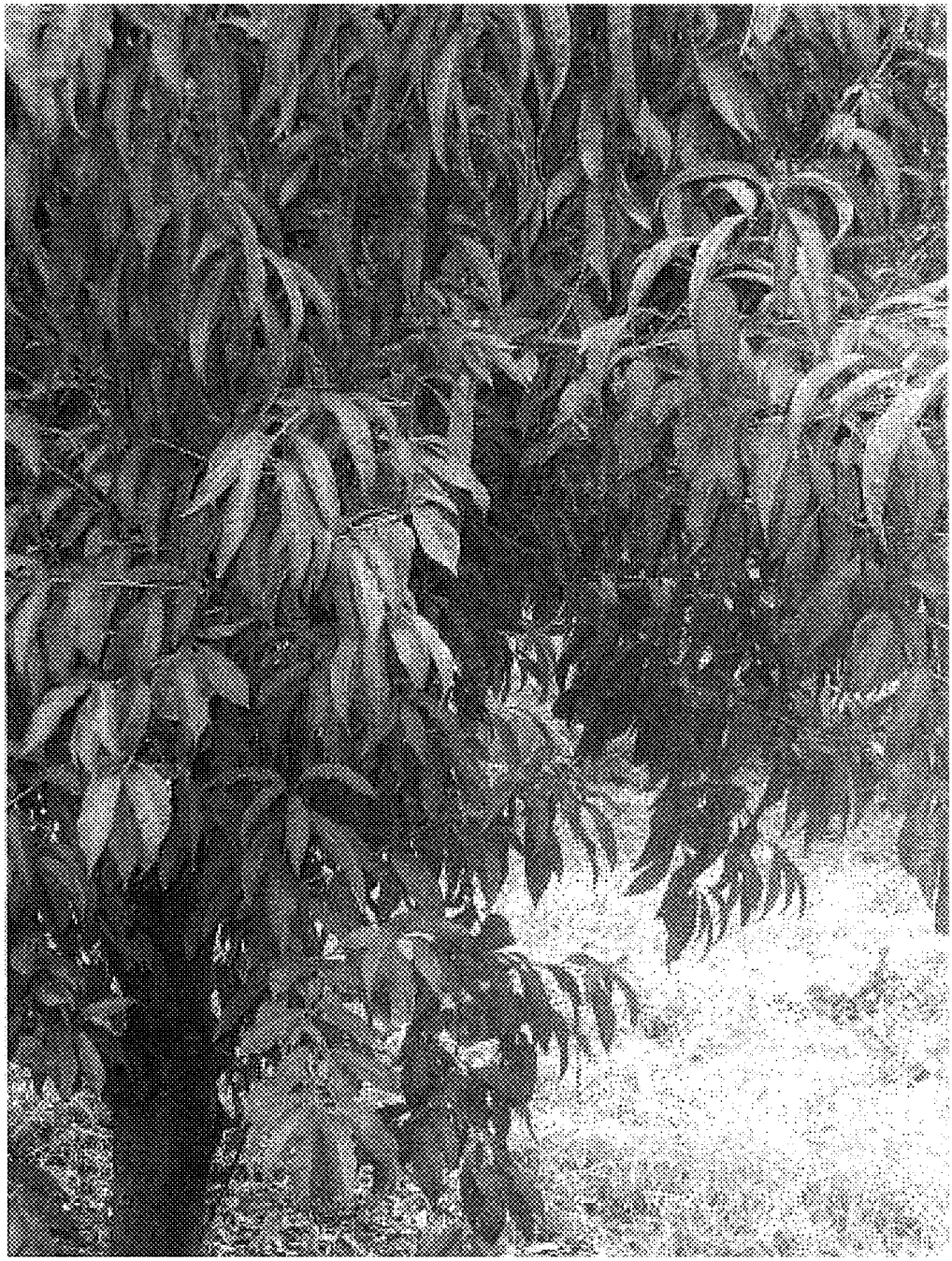
FIG. 3 shows a tree of the new variety.

The following detailed botanical description is based on observations made during the 2005 growing season at Parker, Wash., of six year old trees grown on Lovell rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant, or any group of plants, of the new variety may vary from the stated average.

Tree: Habit — moderate spreading; Vigor — moderate; Size — height 4 m, width 2.5 m; Trunk — diameter 22 cm at soil level, texture rough, color greyed-red 178A, over color grey 201D, lenticels inconspicuous; Branches — color brown N199D, green 145A at tip, crotch angle 80°; Heat and cold tolerance — tolerant in area observed (USDA hardiness zone 6).

Dormant one-year-old shoot: Size — diameter 0.4 cm, length 24 cm; Color greyed-purple 183A; Internode length 2 to 3 cm; Lenticels inconspicuous; Not pubescent.

Leaves: Size — length 13 cm, width 3.5 cm; Shape lanceolate, margin serrate, texture smooth; Color green 146B; Petiole — length 12 mm, diameter 2 mm, color greyed-orange 173A.

Flowers: Bud — length 1.5 cm, diameter 0.7 cm, shape rounded, color red-purple N57D, tip red-purple 73C; Flower size — diameter 4 cm; Petals — 5 per flower, overlapping, length 1.8 cm, width 1.5 cm, margin smooth, color upper surface red-purple 73D, lower surface red-purple N57D; Sepals — 5 per flower, smooth, shape narrow with rounded tip, length 0.7 cm, width 0.5 cm, color red-purple 59B; Pedicel — length 0.4 cm; color yellow-green 154A; Anthers — 23 per flower, length 1 mm; Filament — length 1 cm; Pollen — scarce, color yellow-green 154A; Stigma — length 0.1 cm, color yellow-green 154B; Style — length 1.2 cm, color red-purple 68D; Ovary — length 0.5 cm, color yellow-green 154B; First bloom March 16, full bloom March 21 (2005 growing season, Parker, Wash.

Fruit: Size — diameter 8 cm, height 4.5 cm; Shape — broad oblate, suture pronounce; Eye — oval, 1.0 cm by 0.5 cm; Stalk — length 0.5 cm, color brown 200D, cavity depth 0.5 cm, width 1.0 cm; Skin — finely pubescent, smooth, no tendency to crack, ground color yellow 13C, over color greyed-orange 168A near top of fruit, greyed-red 179A near bottom, overcolor on 90% of fruit surface in a solid blush pattern; Flesh — fine texture, soft, very juicy, sweet, mild aroma color yellow-orange 21B; Stone — round to oval, diameter 2 to 2.5 cm, color orange-red N34A, texture ridged, no tendency to split; Freestone; Kernel — heart shaped with rounded base, length 1 cm, width 1 cm, color orange 26B with greyed-orange 177C stripe; Pressure — 4.5 to 7.5; Brix — 13.

Market use: Fresh market, will maintain quality in cold storage for 3 to 4 weeks.

Resistance to known diseases: None noted.

It is claimed:

1. We claim a new and distinct peach tree substantially as shown and described herein.

* * * * *

UNITED STATES PATENT AND TRADEMARK OFFICE

CERTIFICATE OF CORRECTION

PATENT NO. : PP 17,457 P3
APPLICATION NO. : 11/013507
DATED : February 27, 2007
INVENTOR(S) : Rene Francois Monet It is certified that error appears in the above-identified patent and that said Letters Patent is hereby corrected as shown below:

Column 3,
Line 20, "zone 6" should read --zone 2--.

Signed and Sealed this

Twenty-fourth Day of April, 2007

JON W. DUDAS
*Director of the United States Patent and Trademark Office*